United States Patent [19]
Pfingstl et al.

[11] Patent Number: 5,117,673
[45] Date of Patent: Jun. 2, 1992

[54] PROCESS AND DEVICE FOR DETERMINING THE SOOT CONTENT OF COMBUSTION GASES

[75] Inventors: Max Pfingstl; Alfred O. Jaschek, both of Graz, Austria

[73] Assignee: AVL Gesellschaft für Verbrennungskraftmaschinen und Messtecknik mbH, Graz, Austria

[21] Appl. No.: 439,027

[22] PCT Filed: May 16, 1988

[86] PCT No.: PCT/AT88/00032
§ 371 Date: Nov. 2, 1989
§ 102(e) Date: Nov. 2, 1989

[87] PCT Pub. No.: WO88/09492
PCT Pub. Date: Dec. 1, 1988

[30] Foreign Application Priority Data
May 19, 1987 [AT] Austria .................. A1276/87

[51] Int. Cl.⁵ .................................. G01N 31/22
[52] U.S. Cl. ........................ 73/28.01; 422/88; 422/91
[58] Field of Search ............... 73/28.01; 422/88, 91

[56] References Cited

U.S. PATENT DOCUMENTS 4,023,930 5/1977 Blunck et al. .................. 422/91
4,115,067 9/1978 Lushkow ........................ 422/91

FOREIGN PATENT DOCUMENTS 267232 12/1968 Austria .
1539930 8/1968 France .
203837 10/1985 Japan .

Primary Examiner—Hezron E. Williams
Assistant Examiner—Craig Miller
Attorney, Agent, or Firm—Watson, Cole, Grindle & Watson

[57] ABSTRACT

In order to obtain a high precision of measurement, which is independent of the soot content of the exhaust gas to be tested in a given process, the proposal is put forward that the volume of exhaust gas taken for each loading of the filter be determined by means of a suitable algorithm from the value of filter blackening obtained in a previous test, sampling being continued if the blackening of the filter is outside a specified range.

17 Claims, 1 Drawing Sheet

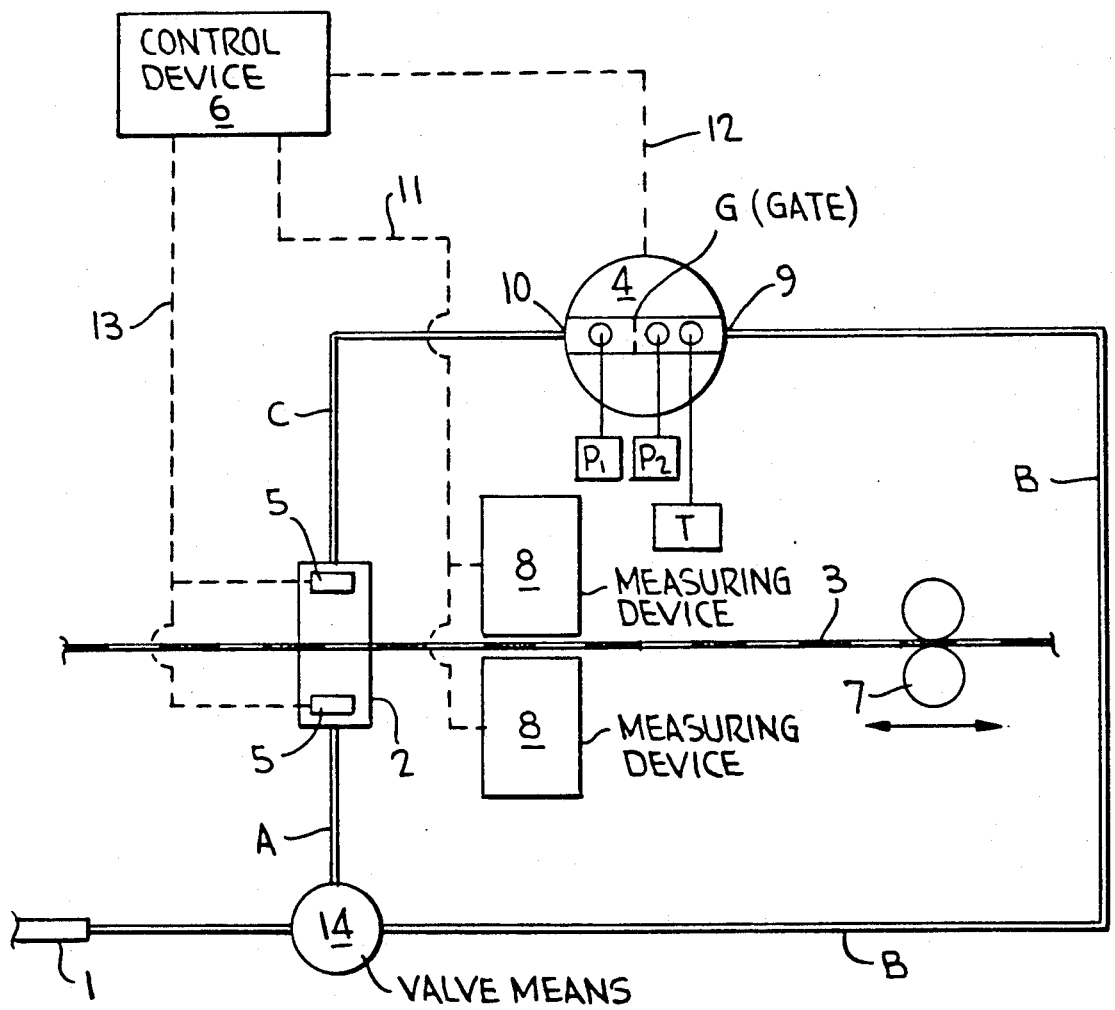

PROCESS AND DEVICE FOR DETERMINING THE SOOT CONTENT OF COMBUSTION GASES

BACKGROUND OF THE INVENTION

This invention relates to a process for determining the soot content of combustion gases, in particular the exhaust gases of internal combustion engines, which will form deposits on, i.e. blacken, a filter through which they are passed, this blackening of the filter being subsequently measured, and to a device for implementing this process.

DESCRIPTION OF THE PRIOR ART

Such a process is described in AT-PS 267 232, for example. In this instance a predetermined quantity of exhaust gas is passed through the filter, whose blackening is then measured. As the measuring equipment used must be suitable for a comparatively wide measuring range and the sensitivity of the equipment is not constant over the entire range, the precision of measurement depends on the soot content of the exhaust gas to be analyzed.

Another process for measuring exhaust gases and a device for implementing this process is presented in DD-PS 127 256. In order to compensate for differences in whiteness of a paper filter tape in the blackened area and in a reference area, the filter tape is subdivided into two parts along its length, one of which is continuously exposed to the samples whereas the adjacent part remains unexposed and is used for reference measurement. The samples of exhaust gas are taken quasi-continuously. The photoelectric evaluation unit has a mask with two openings, one of which is directed towards a part of the filter tape subject to the exhaust gas, whereas the other one is directed towards an unexposed part of the tape situated beside the former. For the same reasons as above the precision of measurement again depends on the soot content of the exhaust gas to be analyzed.

SUMMARY OF THE INVENTION

It is an object of the invention to propose a process of the above kind in which the precision of measurement will remain constant, regardless of the soot content of the exhaust gas to be analyzed.

In the invention this is achieved by determining by means of a suitable algorithm the volume of exhaust gas taken for each loading of the filter from the value of filter blackening obtained in a previous test, sampling being continued if the blackening of the filter is outside a specified range. In this manner the devices provided for measuring filter blackening may be used within a predetermined range, thus preventing the device characteristic from entering into the measurement.

It is recommended to operate in a range of relatively strong blackening since in this case differences in the whiteness of the filter material, e.g. a filtering paper, will not have any noticeable influence on the test result.

According to another aspect of the invention the exhaust volume may be determined upon its passage through the filter, and the resulting value may be combined with the value obtained for the blackening of the filter in a suitable computing device in such a way as to generate a signal proportional to the soot content in the exhaust gas. In this way the process may be organized in a simple manner which will also permit automation.

For further improvement of the precision of measurement it is proposed in a modified version of the invention that the pressure and/or temperature of the exhaust gas passing through the filter be measured and the volume of the exhaust gas passed through the filter during each measuring cycle be compensated for pressure and/or temperature.

In further development of the invention the proposal is put forward that the blackening of the filter be examined after a first sampling, and another sampling and measuring cycle be initiated automatically if the blackening of the filter is outside a specified range. With the use of a computing device this kind of process may easily be performed with conventional means.

It may further be provided that the blackening of the filter be continuously monitored throughout the sampling process by one or more sensors, and that sampling be terminated when the blackening is within a specified range. In this way one step of the procedure may be eliminated. In this variant of organizing the process the volume of exhaust gas passed through the filter is controlled by a rough and continuous testing of the degree of blackening.

The invention also permits that the same sample volume be used for each individual sample and that the blackening be checked after the passage of each individual volume, the sampling process being terminated when the blackening of the filter is within a specified range, and a given volume being sucked through repeatedly, i.e. at certain intervals, until a certain degree of blackening has been reached.

For instance, sampling may be continued until the blackening amounts to 20-50% of the absolute blackening of the filter.

It is recommended to automatize all steps and sequences of the procedure.

It is another object of the invention to describe a device for implementing the process specified by the invention.

AT-PS 267 232 presents a device where a sampling line connected with a channel conveying the exhaust gas to be analyzed, leads to a sampling device and a filter through which is passed a tape of filter paper, which is advanced stepwise and is controlled by a feed mechanism, and where a photoelectric measuring unit is provided, through which the tape of filter paper may be passed and which is located behind the filter in the direction of tape advance.

In this known device the volume passed through the filter during a measurement cycle is predetermined.

Based on this type of device the proposal is put forward in another variant of the invention that the sampling device, which is provided with a measuring device determining the volume or quantity of exhaust gas, and the device for measuring the blackening of the filter paper be coupled to a control device comprising a computing element, which will calculate from the blackening value of the filter paper the volume of exhaust gas required for obtaining meaningful test results, using a particular algorithm, and which will then deliver an appropriate signal to the sampling device. This kind of device will ensure that the volume of exhaust gas required for sufficient blackening is determined before the measuring process takes place. For this purpose the degree of blackening obtainable from a given volume of exhaust gas is measured, on the basis of which the volume of exhaust gas is determined which is required for obtaining a blackening within a specified range. The control device will ensure an automated sequence, the filter being exposed to a defined quantity of exhaust gas, subsequent to which the degree of blackening will be determined in the device for measuring the blackening values. From these values the required volume of exhaust gas may be calculated by the computer in the control device, and the sampling device may be suitably controlled when the filter is subjected to a new load of exhaust gases, their volume now being sufficient for obtaining a blackening value within the specified range.

According to another characteristic of the invention the sampling device, which is provided with a device for measuring the volume or quantity of exhaust gas, and the device for measuring the blackening of the filter paper may be connected with a control device, and an additional photoelectric measuring unit may be provided in the housing of the filter, which is connected to the control device comprising a comparator for comparing the signals arriving from the photoelectric measuring unit with a predetermined value, which comparator will generate a signal de-activating the sampling device as soon as a preset threshold value has been reached. In this variant the exhaust gas is passed through the filter until the filter tape has reached a degree of blackening sufficient for precise measurement. This will permit a rapid and uncomplicated measuring process.

In order to ensure rapid and precise volume measurings the invention proposes that the volume or quantity measuring device be provided with a pressure sensor as well as a gate located in the stream of exhaust gas, pressure sensors being situated on either side of the gate and a temperature sensor also being placed in the area of the gate. With this arrangement the pressure before ($p_1$) and after ($p_2$) the gate may be measured, and the exhaust gas volume may be determined from the pressure difference $\Delta p = p_1 - p_2$, and from $p_1$ or $p_2$ and the known geometry of the gate, the temperature T and the density $\rho$ being accounted for.

Besides, the sampling device may be connected with the exhaust gas channel by means of a direct line and a line going via the filter, these lines being made to connect alternatingly with the pressure side and the suction side of the sampling device, and the measuring heads being located on either side of the filter tape. In this way the exhaust gas may either be sucked or pressed through the filter.

In this context it will be of advantage if one photoelectric measuring unit is installed on each side of the filter tape in the filter housing, which will eliminate the need for re-installing the measuring units in case of a reversal of the direction in which the filter is exposed to the exhaust gases.

DESCRIPTION OF THE DRAWINGS

Following is a more detailed description of the invention as illustrated by the accompanying drawing, which presents a schematical view of a device for implementation of the process described by the invention.

From the exhaust gas channel 1 the exhaust gas is passed through a sampling line B to the sampling device 4, a measuring line A branching off from the sampling line B at valve means 14, and leading to a filter 2. This filter is also connected to the sampling device 4 by a line C. The outlets 9 and 10 of the sampling device 4, which are connected with lines B and C, may be operated in suction or pressure mode, such that the exhaust gas may be sucked or pressed through the filter.

For volume measurement the sampling device 4 may include a gate in the stream of exhaust gas, and pressure sensors located in front of the gate and behind it and a temperature sensor may be used for determining the exhaust volume as a function of $\Delta p$, $p$ and T.

The filter 2 itself essentially comprises a housing through which a filter tape 3 made of filter paper or some other filter material may be passed. The tape 3 is moved by a drive unit 7 which may be controlled by the control device 6 for a step-wise advance of the filter tape.

In the moving direction of the tape photoelectric measuring devices 8 are installed at a distance of the filter 2, which are used for determining the blackening value of the filter tape. These measuring devices 8 as well as the sampling device 4 are connected to the control device 6 via electric lines 11 and 12, the control device receiving signals corresponding to the blackening of the filter tape and to the volume, temperature and pressure of the exhaust gases, i.e. the latter from the sampling device 4, and also sending control signals to the sampling device 4.

The housing of the filter 2 also contains photoelectric measuring units 5, which are located on either side of the filter tape 3 and are also connected to the control device via the electric line 13. By arranging the measuring units 5 and the measuring devices 8 on both sides of the filter tape 3, the exhaust gases may be passed through the filter alternatingly from either side using valve 14.

This device can be operated in two modes.

In the first mode, a defined and predetermined volume of exhaust gas is passed through the filter 2, and the filter tape 3 is advanced by the drive unit 7 by one step, such that the part of the filter tape blackened by the exhaust gas reaches the measuring device 8 for testing. From the signals delivered by the measuring devices 8, or rather, the measuring device 8, as only one is activated at one and the same time, depending on the direction of flow of the exhaust gas through the filter 2, and the predetermined volume of exhaust gas, the computer of the control device 6 will calculate the exhaust gas volume required for obtaining a blackening value within a specified range, and will send an appropriate signal to the sampling device 4. The drive unit 7 is actuated again in order to advance the filter tape by a further step. Since the filter tape is suitably blackened now the blackening value may be determined with great precision.

From the signals delivered by suitable sensors and measuring elements in the sampling device 4, which correspond to the volume of the exhaust gases passed through the filter, their temperatures and pressures, the computer of the control device 6 will also be able to calculate the soot content related to a standardized exhaust gas volume.

In the second mode of operation, the degree of blackening of the filter tape 3 is registered by the photoelectric measuring unit 5 while the exhaust gases pass through the filter 2, no high demands being made as to the precision of this continuous test. Once a specified degree of blackening has been reached, the signals delivered by the unit 5 exceed a threshold value monitored by a comparator of the control device 6, upon which the comparator will emit a signal de-activating the sampling device 4, such that the filter 2 is no longer subject to the exhaust gases. Then the filter tape 3 is advanced by the drive unit 7 until it reaches the measuring devices 8. where the degree of blackening is precisely determined.

From the signals corresponding to the volume of the exhaust gases having passed through the filter and to their temperatures and pressures, the computer of the control device 6 will determine the blackening number or the soot content of a standardized exhaust gas volume.

We claim:

1. A process for determining the soot content of combustion gases, comprising the steps of:
   (a) passing a first portion of said combustion gases through a first filter portion to blacken said first filter portion with soot,
   (b) measuring the blackening of said first filter portion to obtain a first measured blackening value,
   (c) comparing said first measured blackening value to a predetermined blackening value range,
   (d) if the first measured blackening value obtained in step (c) is outside said predetermined blackening value range, automatically passing a second portion of said combustion gases through a second filter portion to blacken said second filter portion with soot and measuring the blackening of said second filter portion to obtain a second measured blackening value which is within said predetermined blackening value range,
   (e) determining the volume of combustion gases which passed through the filter that provided a measured blackening value within said predetermined blackening value range, and
   (f) calculating the soot content of said combustion gases from the measured blackening value within said predetermined blackening value range and the volume of combustion gases determined in step (e).

2. A process according to claim 1, wherein a defined sample volume is used for each individual sample, said volume is sucked through repeatedly, and wherein the blackening is checked after passage of each individual sample, the sampling process being terminated as soon as the blackening of said filter is within said specified range.

3. A process according to claim 1, including measuring temperature and pressure values of the portion of combustion gases passed through said filter portions which provided a measured blackening value within said predetermined blackening value range, and utilizing said temperature and pressure values in said calculating accomplished in step (f).

4. A process according to claim 1, wherein said predetermined blackening value range is 20 to 50% of absolute blackening of said filter portions.

5. A process for determining the soot content of combustion gases, comprising the steps of:
   (a) passing said combustion gases through a filter to blacken said filter with soot,
   (b) determining the volume of said combustion gases passed through said filter,
   (c) simultaneously with steps (a) and (b), measuring the blackening of said filter to obtain a measured blackening value,
   (d) continuing steps (a), (b) and (c) until said measured blackening value is within a predetermined blackening value range, and
   (e) determining the volume of combustion gases which have passed through said filter during steps (a)-(d), and
   (f) calculating said soot content from said measured blackening value of step (d) and the volume of said combustion gases determined in step (e).

6. A process according to claim 5, including measuring the temperature and pressure values of said combustion gases passing through said filter in steps (a) and (d) and including said temperature and pressure values in said calculating accomplished in step (f).

7. A process according to claim 5, wherein said predetermined blackening value range is 20 to 50% of absolute blackening of said filter.

8. A process according to claim 5, wherein filter blackening is continuously monitored by at least one sensor.

9. A device for determining the soot content of combustion gases passing through a channel, said device comprising:
   a filter apparatus which includes a housing and a filter tape which passes through said housing,
   a drive unit for moving said filter tape through and downstream of said housing in a stepwise fashion,
   a sensor means located downstream of said housing for measuring the blackening of said filter tape,
   a sample line which conveys said combustion gases containing soot from said channel to said housing so as to pass through said filter tape in said housing and deposit soot thereon, thereby blackening said filter tape,
   a sampling means for measuring the volume of combustion gases which pass through said filter tape in said housing, and
   a control means connected to said sampling means and to said sensor means for causing a sufficient volume of combustion gases to be passed through said sampling means and said filter tape to deposit an amount of soot on said filter tape within a predetermined blackening value range, based on a prior measurement of blackening of said filter tape, and including a computing means for providing a soot content value of said combustion gases.

10. A device according to claim 9, wherein said sampling means includes a gate and temperature and pressure sensors for determining the temperature and pressure of said combustion gases.

11. A device according to claim 9, wherein said filter tape divides said housing into opposite first and second portions, and wherein said sample line includes a valve means, a first branch line for delivering combustion gases from said multiway valve to said first portion of said housing and a second branch line for delivering combustion gases from said valve means to said sampling device and from said sampling device to said second portion of said housing.

12. A device according to claim 11, wherein said sensor means comprises separate photoelectric measuring devices located on opposite sides of said filter tape.

13. A device for determining the soot content of combustion gases passing through a channel, said device comprising:
   a filter apparatus which includes a housing and a filter tape which passes through said housing,
   a drive unit for moving said filter tape through and downstream of said housing in a stepwise fashion,
   a first sensor means located in said housing for measuring the blackening of said filter tape in said housing, a second sensor means located downstream of said housing for measuring the blackening of said filter tape, a sample line which conveys said combustion gases containing soot from said channel to said housing so as to pass through said filter tape in said housing and deposit soot thereon, thereby blackening said filter tape, a sampling means for measuring the volume of combustion gases which passes through said filter tape in said housing, and a control means connected to said sampling means, to said first sensor means and to said second sensor means, said control means including a comparator and functioning to de-activate said sampling means when said first sensor means detects a blackening of said filter tape in excess of a threshold value, to move said filter tape such that the blackening thereof can be precisely measured by said second sensor means, and to provide a soot content value of said combustion gases based on the volume of combustion gases which have passed through said filter tape and the precisely measured blackening of said filter tape.

14. A device according to claim 13, wherein said sampling means includes a gate and temperature and pressure sensors for determining the temperature and pressure of said combustion gases.

15. A device according to claim 13, wherein said filter tape divides said housing into opposite first and second portions, and wherein said sample line includes a valve means, a first branch line for delivering combustion gases from said multiway valve to said first portion of said housing and a second branch line for delivering combustion gases from said multiway valve means to said sampling device and from said sampling device to said second portion of said housing.

16. A device according to claim 15, wherein said first sensor means comprises separate first and second photoelectric measuring devices respectively located in first and second portions of said housing.

17. A device according to claim 16, wherein said second sensor means comprises separate third and fourth photoelectric measuring devices located on opposite sides of said filter tape.

* * * * *

UNITED STATES PATENT AND TRADEMARK OFFICE
CERTIFICATE OF CORRECTION

PATENT NO.  : 5,117,673
DATED       : June 2, 1992
INVENTOR(S) : Max PFINGSTL et al.

It is certified that error appears in the above-identified patent and that said Letters Patent is hereby corrected as shown below:

On the Title page, item

[73] Assignee: AVL Gesellschaft für Verbrennungskraftmaschinen und Messtechnik MBH Prof.Dr.Dr.h.c. Hans List, Graz, Austria Signed and Sealed this Seventeenth Day of August, 1993

Attest:

BRUCE LEHMAN

*Attesting Officer*     *Commissioner of Patents and Trademarks*